(12) United States Patent
Taylor

(10) Patent No.: US 6,831,104 B2
(45) Date of Patent: Dec. 14, 2004

(54) INSECT PEST ERADICATION SYSTEM

(76) Inventor: Tommy G. Taylor, 4011 Creole St., Lake Charles, LA (US) 70605

(*) Notice: Subject to any disclaimer, the term of this patent is extended or adjusted under 35 U.S.C. 154(b) by 0 days.

(21) Appl. No.: 09/969,329

(22) Filed: Oct. 2, 2001

(65) Prior Publication Data

US 2003/0053955 A1 Mar. 20, 2003

Related U.S. Application Data

(60) Provisional application No. 60/237,455, filed on Oct. 2, 2000.

(51) Int. Cl.[7] ............ A61K 31/11; A61K 31/035; A01N 29/02

(52) U.S. Cl. ................................ 514/693; 514/746

(58) Field of Search ................. 514/693, 746, 514/247, 744; 424/405

(56) References Cited

U.S. PATENT DOCUMENTS

| | | | | |
|---|---|---|---|---|
| 3,524,911 A | * | 8/1970 | Leavitt | 424/45 |
| 3,845,172 A | | 10/1974 | Magee | 260/956 |
| 4,595,679 A | * | 6/1986 | Broadbent | 514/67 |
| 4,626,528 A | | 12/1986 | McHenry | 514/119 |
| 5,104,659 A | | 4/1992 | Fishbein et al. | 615/611 |
| 5,278,163 A | | 1/1994 | Ogura et al. | 514/252 |
| 5,620,678 A | | 4/1997 | Burke | 424/45 |
| 5,693,344 A | * | 12/1997 | Knight et al. | 424/687 |
| 5,897,859 A | | 4/1999 | Vander Meer et al. | 424/84 |

* cited by examiner

*Primary Examiner*—Alton Pryor
(74) *Attorney, Agent, or Firm*—Henry E. Naylor

(57) ABSTRACT

An insect pest eradication system comprised of a non-lethal knockout agent and an insecticide. The present invention also relates to a method of eradicating insects, particularly those found in earthen colonies, by treating the insects with a non-lethal knockout agent, such as trans-dichloroethylene, in combination with a suitable insecticide for the targeted insects.

10 Claims, No Drawings

INSECT PEST ERADICATION SYSTEM

This application claims benefit of Provisional Application No. 60/237,455 filed Oct. 2, 2000.

FIELD OF THE INVENTION

The present invention relates to an insect pest eradication system comprised of a non-lethal knockout agent and an insecticide. The present invention also relates to a method for eradicating insects, particularly those found in earthen colonies, by treating the colony with a non-lethal knockout agent, such as trans-dichloroethylene, in combination with a suitable insecticide for the targeted insects.

BACKGROUND OF THE INVENTION

Non-indigenous insect pest infestations present a significant problem to homeowners, landowners, livestock and vegetation in the warmer regions of the United States. For example, the Red Fire Ant (fire ant) proliferates across the South and has more recently begun to invade parts of Southern California. The fire ant lives in colonies comprised of at least several thousands of individuals. Some colonies have been known to contain up to about 500,000 or more ants. When their dirt mounds are disturbed, the ants swarm upon the invader delivering relentless and extremely painful stings. In humans, the stings cause itching welts that may last for many days. Scratching the wounds may lead to infection and some persons may even suffer severe allergic reactions. Small children unfamiliar with the habits of the fire ant are particularly susceptible to attack. The fire ant provides an even greater danger to livestock. Fire ant mounds dot most pastures in the Southern United States and cattle frequently suffer from ant attacks. Abundant fire ant stings may, in fact, kill calves. Vegetation is also susceptible to depletion by foraging fire ants. Furthermore, fire ants that have infested agricultural fields pose a threat to humans harvesting crops. Damage due to fire ants is estimated at tens of millions of dollars annually.

A common method currently in use for controlling fire ants involves the application of granules coated with a water-soluble poison directly onto a fire ant mound, and then gently dousing the mound with water, so that the poisonous coating is dissolved and carried into the colony. One brand of such product, Spectracide®, which is comprised of Diazinon® ($C_{12}H_{21}N_2O_3PS$), advertises that it will kill fire ants within 24 hours. Unfortunately, the technique is somewhat ineffective. Individual insects may be observed moving actively about the targeted colony when the insecticide granules and/or water are applied. Furthermore, new fire ant colonies, presumably individuals and an unharmed queen from the targeted colony, have been observed to form in the immediate vicinity of the original mound within 12 hours of the treatment.

Another common technique currently employed for controlling the fire ant problem involves the use of "baiting" systems, wherein a poison is implanted into a fire ant food source, which is carried back into the fire ant colony by worker ants. This technique, while considered environmentally advantageous, has the distinct disadvantage of being relatively slow acting when compared to direct application of insecticide to the fire ant colony. For example, one of the faster-acting "baits" is Amdro®, which is comprised of hydramethylnon and has the chemical name tetrahydro-5,5-dimethyl-2(1H)-pyrimidinone {3-{4-(trifluoromethyl) phenyl}-1-{2-{4-trifluoromethyl) phenyl}ethenyl}-2-propenyl-idene}hydrazone. When it is broadcast it is reported to have a maximum 80%–90% effectiveness rating in 3 to 8 weeks. In such time, it is highly probable that the rapidly propagating fire ant would establish new colonies not far from baited sites. Furthermore, a "baiting" system is always subject to the foraging whimsy of the individual fire ant. When other food sources are accessible fire ants may not even seize the bait. In addition, these baits are always subject to dilution and/or dispersion by rains and flooding, potentially rendering them ineffective in targeted areas.

Certain chlorinated hydrocarbons have been used in the past for controlling insect pests such as the fire ant. U.S. Pat. No. 5,104,659 to Fishbein discloses a wide variety of insecticides, including "chlorinated hydrocarbons." U.S. Pat. No. 5,897,859 to Vander Meer discloses that fire ant problems in agricultural areas were largely suppressed "through the wide scale use of residual chlorinated hydrocarbon insecticides from 1950 to 1970," but that use of these "highly effective insecticides" largely ceased because of environmental concerns. U.S. Pat. No 4,626,528 to McHenry discloses that "the only truly successful toxicant for the control of fire ants and termites has been Mirex, a chlorinated hydrocarbon" but that "this material has been withdrawn from use because of concerns over its toxicity in certain animals and its unusual stability in the environment."

Furthermore, chlorinated compounds have been used as carriers and solvents in insecticides. For example U.S. Pat. No. 5,278,163 to Ogura, et al. discloses that chlorinated hydrocarbons may be used as carriers for pesticidal compounds. U.S. Pat. No. 3,678,168 to Grier specifies that chlorinated hydrocarbons such as "chloroform, carbon tetrachloride and tetrachloroethylene" may serve as suitable carriers for pesticidal compounds. Also, U.S. Pat. No. 5,620,678 to Burke discloses that "(h)alogenated solvents, such as methylene chloride and 1,1,1-trichloroethane are common carriers, diluents and solvents for aerosol sprays" used to eradicate crawling and flying insect pests, but that these applications "have been restricted due to health and environmental concerns." All of the above mentioned patents are incorporated herein by reference.

While there are many commercially available insecticide systems for killing insects, particularly those that colonize in great numbers, there is a need in the art for systems that are more effective for killing substantially all insects in a colony.

SUMMARY OF THE INVENTION

An insecticide delivery system comprising an effective amount of a non-lethal knockout agent and an effective amount of an insecticide.

In a preferred embodiment the insecticide delivery system of claim 1 wherein the knockout agent is selected from the group consisting of cis-dichloroethylene, trans-dichloroethylene, trichloroacetaldhyde, trichloroacetaldhyde hydrate, chloral, and chloral hydrate.

In another preferred embodiment the insect is a fire ant, the insecticide is selected from Diazinon® and hydramethylnon, and the knockout agent is trans-dichloroethylene.

In still another preferred embodiment the knockout agent and the insecticide are blended together and applied to the insect infestation together.

DETAILED DESCRIPTION OF THE INVENTION

The invention described herein relates to the use of an effective amount of one or more non-lethal knockout agents in combination with an effective amount of one or more insecticides. By "effective amount" of knockout agent we mean at least that minimum amount needed to incapacitate the targeted insects at application conditions. By "effective amount" of insecticide we mean at least that minimum amount needed to kill the incapacitated insects at application conditions. The most preferred knockout agent is trans-dichloroethylene, particularly when used for certain insect pests, such as the imported Red Fire Ant. Trans-dichloroethylene, whether pure or blended with other components, can render these insect pests inert long enough for effective amounts of a suitable poison to make contact with, and kill, the inert individual insects. Trans-dichloroethylene has the advantage over other chemical compounds, particularly chlorinated hydrocarbons, that have been used in insecticide applications in that it does not pose a lasting threat to the environment.

The present invention relates to a multi-agent insecticide system for killing a substantial number of insects of an infestation. Non-limiting examples of infestations include earthen mounds, nests, hives, colonies, swarms, and clusters. Conventional insecticide applications relate to the use of certain chlorinated hydrocarbons as carriers, or solvents, for insecticides, or as insecticides themselves. None of the conventional insecticides that are based on chlorinated hydrocarbons are benign to the environment. Chlorinated hydrocarbons used in conventional insecticide applications are generally highly stable molecules that are not readily decomposed in the lower atmosphere. The inventor hereof has unexpectedly discovered that a substantial number, preferably substantially all, insects in an infestation are killed by use of a non-lethal knockout agent in combination with an insecticide. The term "knockout" or "non-lethal knockout" as used herein means that the insects are rendered incapacitated or inert, but still alive. It will be understood that the terms "incapacitated", "immobilized", and "inert" are used interchangeably herein. If an insecticide is not used in combination with the knockout agent the insects will eventually return to a normal active state. The knockout agents of the present invention are capable of incapacitating the insects for up to 2 or more hours. This allows sufficient time for an insecticide to be applied to kill them. The use of the knockout agents of the present invention allow one to use more environmentally acceptable insecticides since the insecticides themselves are not expected to instantly knockdown the insects. To kill substantially all insects of a colony without the use of combination knockout agent/insecticide one would need to use very powerful environmentally unacceptable insecticides. Such insecticides are increasing being taken off the consumer market.

Any suitable knockout agent can be used in the practice of the present invention. By knockout agent we mean a chemical composition, when in contact with a target insect, will leave that insect incapacitated, but not dead. Typically, once the insects have been in contact with the knockout agent they will be incapacitated for a finite period of time. If an insecticide is not applied they will recover and presume its normal activity. Although the knockout agent is effective in a liquid as well as vapor form, it is preferred that the target insects be subjected to the vapor form. It has been found that substantially all of the insects of an infestation can be eradicated by first incapacitating them with a knockout agent, then contacting them with an insecticide. Incapacitation can take the form of either unconsciousness or merely slowing the insects so they do not escape the target area of insecticide application. Preferred knockout agents suitable for use in the practice of the present invention are those that possess properties that make them suitable for use in the present invention. Such suitable properties include: 1) its volatility, thus permitting the rapid formation of vapors that are preferably heavier than air; 2) its ability to render insect pests immobile for up to several hours; 3) its instability in the environment, thus ensuring its decomposition within an acceptable period of time; and 4) its insolubility in water, thus permitting its evaporation and escape into the atmosphere after the targeted insects are soaked with poisonous water.

Non-limiting examples of preferred knock-out agents include dichloroethylene isomers, such as cis-dichloroethylene and trans-dichloroethylene; trichloroacetaldhyde ($C_2HCl_3O$), including its hydrate form ($CCl_3CH(OH)_2$; chloral and chloral hydrate. The most preferred knockout agent is trans-dichloroethylene, particularly when the insects are fire ants. In tests conducted by the inventor hereof, trans-dichloroethylene, when applied superficially to a fire ant mound, proved effective in rendering substantially all individual insects in the targeted fire ant mound completely incapacitated until a suitable poison could make contact with, and kill, all individual insects, most notably the fire ant queen. In tests conducted by the inventor hereof, trans-dichloroethylene, when applied superficially to a fire ant mound, proved effective in rendering substantially all individual insects in the targeted fire ant mound completely incapacitated until a suitable poison could make contact with, and kill, all individual insects, most notably the fire ant queen.

A diluent can be used in combination with the knockout agent. The diluent can be an organic compound in which the knockout agent is at least partially soluble or miscible, preferably substantially entirely soluble or miscible. Non-limiting examples of diluents include: (1) oils, preferably biodegradable vegetable oils; (2) alcohols, such as methyl alcohol, ethyl alcohol, n-propyl alcohol, iso-propyl alcohol, n-butyl alcohol, sec-butyl alcohol, t-butyl alcohol, iso-butyl alcohol, furfuryl alcohol, and tetrahydrofurfuryl alcohol; (3) ketones or ketoalcohols such as acetone, methyl ethyl ketone and diacetone alcohol; (4) ethers, such as tetrahydrofuran and dioxane; (5) esters, such as ethyl acetate, ethyl lactate, ethylene carbonate and propylene carbonate; (6) polyhydric alcohols, such as ethylene glycol, diethylene glycol, triethylene glycol, propylene glycol, tetraethylene glycol, polyethylene glycol, glycerol, 2-methyl-2,4-pentanediol 1,2,6-hexanetriol and thiodiglycol; (7) lower alkyl mono- or di-ethers derived from alkylene glycols, such as ethylene glycol mono-methyl (or -ethyl) ether, diethylene glycol mono-methyl (or -ethyl) ether, propylene glycol mono-methyl (or -ethyl) ether, triethylene glycol mono-methyl (or -ethyl) ether and diethylene glycol di-methyl (or -ethyl) ether; (8) nitrogen containing cyclic compounds, such as pyrrolidone, N-methyl-2-pyrrolidone, and 1,3-dimethyl-2-imidazolidinone; and (9) sulfur-containing compounds such as dimethyl sulfoxide and tetramethylene sulfone. Water can also be used as the diluent. More preferred are alcohols, biograдеable oils, and water. Most preferred are alcohols and water, particularly water.

Any insecticide that is a poison to the targeted insects can be used in the practice of the present invention. Non-limiting examples of such insecticides include the organochlorines (chlorinated hydrocarbons) which includes diphenyl aliphatics, hexchlorocyclohexane, cyclodienes, polychloroterpenes, and the like; the organophosphates inclusive of aliphatics such as malathion, phenyl derivatives such as the alkyl parathions, and heterocyclic derivatives such as Diazinon®; the organosulfurs such as tetradifon, propargite, and ovex; the carbamates that are derivatives of carbamic acid such as carbaryl; the dinitrophenols such as binapacryl and 2,4-dinitrophenol; the organotins such as cyhexatin; the pyrethroids such as permethrin, allethrin, tetramethrin, fenvalerate, cypermethrin, flucythrinate, fluvalinate, deltamethrin, and bifenthrin; the nicothinoids such as imidacloprid; the spinosyns such as spinosad which is a mixture of spinosyns A and D; the fiproles or phenylpyraxoles such as fipronil; the pyrroles such as chlorfenapyr; the pyrazoles such as tebufenpyrad; the phridazinones such as pyridaben; the quinazolines such as 4-[[4-(1, 1-dimethylethyl)phenyl]ethoxy]quinazoline; the benzoylureas such as triflumuron and diflubenzuron; the botanicals such as pyrethrum, nicotine, rotenone, and d-limonene; the synergists such as piperonyl butoxide; the antibiotics such as the avermectins and emamectin benzoate; the fumigants such as sulfuryl fluoride and the like; the inorganics such as inorganic fluorides like sodium fluoride; barium fluoride, and crylite; as well as miscellaneous compounds such as pyriproxyfen, buprofezin, clofentezine, sodium tetrathiobarbonate, hydramethylnon, and the like. A detailed description of such insecticides can be found in The Pesticide Book, by George W. Ware, 5$^{th}$ edition, 2000, Thomson Publications and incorporated herein by reference. More preferred insecticides include organophosphorous (particularly Diazinon®) and pyrethroids (particularly permethrin). It will be understood that any of these insecticides can be used that are effective for the targeted insects. It will also be understood that some of these insecticides are no longer commercially available because of their hazard to the environment, but are never-the-less effective from a technical point of view for eliminating insects. Further, some of these insecticides are only available to licensed professionals and not consumers.

One preferred insecticide class for use in the present invention are organophosphorous compounds including phosphates, phosphoronionates, and phosphorothionates. For example, a suitable, well-known organophosphorous compounds, useful as toxicants in the present invention includes acetylphosphoramidithiotic acid O,S-dimethyl ester, more commonly called "Acephate," and commonly available under the "Ortho" and Orthene" brand names (see also U.S. Pat. Nos. 3,716,600 and 3,845,172, both assigned to Chevron).

Other examples of suitable organophosphorous compounds which have toxic effects toward fire ants, include, but are not limited to, phosphorothioic acid O,O-diethyl O-(3,5,6-trichloro-2-pyridinyl) ester, also known by "Chlorpyrifos", and commercially available under the "Dursban", "Lorsban", and "Pyrinex" brand names (see also U.S. Pat. No. 3,244,586 assigned to Dow Chemical); phosphorothioic acid O,O-diethyl O->6-methyl-2-(1-methylethyl)-4-pyrimidinyl!ester, also known by "Dimpylate", and commercially available under the "Basudin", Diazinon", "Diazol", "Garden Tox", "Sarolex", and "Spectracide" brand names (see also U.S. Pat. No. 2,754,243 assigned to Geigy); phosphorothioic acid O,O-dimethyl O-(3-methyl-4-nitrophenyl) ester, also known by "Fenitrothion", and commercially available under the "Accothion", "Cyfen", Cyten", "Folithion", "MEP", "Metathion" and "Sumithion" brand names (see also Belgian Pat. No. 594,669 to Sumitomo as well as Belgian Pat. No. 596,091 to Bayer); phosphorothioic acid O,O-dimethyl O->3-methyl-4-(methylthio)phenyl!ester, also known by "Fenthion", and commercially available under the "Baycid", "Baytex", "Entex", "Lebaycid", "Mercaptophos", "Queletox", "Spotton", "Talodex" and "Tiguvon" brand names (see also German Patent No. 1,116,656 as well as U.S. Pat. No. 3,042,703, both assigned to Bayer; see also Japanese Pat. No. 15,130, which issued in 1964 to Sumitomo); 4-ethoxy-7-phenyl-3,5-dioxa-6-aza-4-phosphaoct-6-ene-8-nitrile 4-sulfide, also known by "Phoxim", and commercially available under the "Baythion", "Sebacil" and "Volaton" brand names (see also U.S. Pat. No. 3,591,662 assigned to Bayer); and the O,O-dimethyl analog of O->2-(diethylamino)-6-methyl-4-pyrimidinyl!phosphorothioic acid O,O-diethyl ester, also known by "Pirimiphos-methyl", and commercially available under the "Actellic", "Blex", and "Silo San" brand names. (See, e.g., entry numbers 25, 2167, 2968, 3910, 3927, 7251 and 7372, respectively, in "The Merck Index", 10th ed., published in 1983 by Merck & Co., Inc.). Another preferred insecticide is hydramethylnon.

Conventional insect pest eradication techniques for treating a colony of insects are usually ineffective since individual insects can escape the targeted area before the insecticide has made contact and killed substantially all individuals. Use of the knockout agents of the present invention has an advantage over conventional pest eradication techniques because substantially all individual insects in a colony are immobilized by the quickly spreading liquid or vapor knockout agent.

The present invention can be practiced by any suitable technique. For example, the knockout agent can first be applied to an insect nest or mound to immobilize the insects. Since insects, such as fire ants, will move vertically within the mound depending on such things as the temperature profile of the mound, it is preferred that the mound be pierced in one or more locations prior to application of the eradication system. A suitable insecticide can then be applied to kill the immobilized insects. The knockout agent can also be mixed with the insecticide, either before or at time of application and the combination used to treat the insects to be eradicated. If the knockout agent and insecticide are mixed it is also within the scope of this invention that an emulsifier can be used. When an emulsifier is used it can be used in a concentration from about 0.2 to 10 wt. %. Non-limiting examples of suitable emulsifiers include mono-, di- and tri-sorbitan esters; polyoxethylene sorbitan esters; ethoxylated nonionic emulsifiers; propoxylated nonionic emulsifiers and ethyoxylated/propoxylated nonionic emulsifiers.

It is also within the scope of this invention that the knockout agent and insecticide be delivered in aerosol or fogger form. This will allow one to eradicate flying insects, as well as those that reside indoors, such as in attics and basements. One or more conventional propellants can be used for the aerosol in a concentration from about 2 to 80 wt. %, based on the total weight of the ingredients. Amongst the propellants that can be used are non-flammable as well as flammable propellants. It is preferred that non-flammable propellants be used for indoor application. Preferred non-flammable propellants include 1,1,1,2-tetraflouroethane (HFC 134a) and compressed gases, such as carbon dioxide. When tetraflouroethane is used it can be used in amounts up to about 33 wt. % and will render the knockout agent, such as trans-dichloroethylene, non-flammable. Preferred flammable propellants suitable for use herein are hydrocarbons. Non-limiting examples of preferred hydrocarbon propellants include acetylene, methane, ethane, ethylene, propane, propene, n-butane, butene, isobutane, isobutene, pentane, pentene, isopentane, and isopentene. Mixtures of these propellants may also be used. It is also within the scope of this invention to treat fungus infestations with use of conventional fungidicides.

The following examples serve to exemplify a more general description set forth above and are for illustrative purposes only and are not intended to limit the scope of the present invention in any way.

EXAMPLES

The experimental method used herein entailed first preparing a mixture of 1 part trans-dichloroethylene (knockout agent) and 2 parts vegetable oil (liquid Crisco® was the vegetable oil most often used in the test) and then applying the mixture to the surface of an active fire ant mound 12 inches or less in surface diameter. The oil with the knockout agent is preferably biodegradable and miscible with the knockout agent. Units of measure are in pints, with the mixture comprising approximately ½ pint trans-dichloroethylene for every pint of vegetable oil. Approximately one-quarter (¼) pint of the trans-dichloroethylene/vegetable oil mixture was applied to a fire-ant hill about 12-inches in surface diameter.

The next step entailed applying a suitable insecticide to the fire ant mound. The insecticide was a commercially available Diazinon® applied one of two forms onto a fire ant mound that had been treated with the trans-dichloroethylene mixture. The forms of Diazinon® were: 1) as granules (Eliminator® or Spectracide®), with one to two gallons of water being slowly sprinkled across the granules and into the fire ant mound; and 2) a liquid solution of water and Diazinon® concentrate or water that had been used to extract poison from Spectracide® granules). While both methods of applying the insecticide were effective, the application of insecticide in liquid form was preferable due to its ease and efficiency. The liquid was found to soak the colony more quickly and more thoroughly than the granule-water technique.

The inventor hereof normally applied approximately one gallon of the insecticide solution upon and into a targeted fire ant mound. However, before applying the liquid solution of insecticide, the inventor first pierced the mound with a slender steel shaft to a depth of about twelve inches or more in at least five places. This measure facilitated the flow of the liquid poison into the depths of the fire ant colony. Interestingly, when puncturing the mound even three minutes after application of the trans-dichloroethylene mixture, no fire ant activity was observed upon or within the mound.

Following all of these tests, the targeted fire ant colonies were excavated in the form of plugs. These "plugs" of excavated earth that had comprised the fire ant colony measured about 12"×12"×12. The plugs were dissected and the insects observed. Hundreds, if not thousands, of dead individual worker ants, dead ant larvae and eggs were detected. In the deepest portion of the plugs, the queen fire ant was found dead. Occasionally, dead winged fire ants could be found among the exterminated colony. These excavations showed that the insect eradication system of the present invention was effective for eradicating substantially the entire colony of fire ants. No new fire ant mounds could be found in or near the vicinity of the targeted colony even after several days of treatment. This was because no individual fire ants, nor fire ant queens, were able to flee the targeted colonies and establish new colonies.

The methods of this invention can be safely and effectively employed on a wide scale in residential properties, livestock pastures, agricultural fields, golf courses, and other public and private lands to exterminate insect pests, such as the Red Fire Ant. An efficient technique is envisioned where a team of exterminators, either on foot or in vehicles, might treat entire fields, or entire golf courses, at a time. One exterminator, or group of exterminators, would apply the knockout agent, preferably a trans-dichloroethylene mixture onto the target fire ant mound and then flag the mound. Within several minutes, a second exterminator, or group of exterminators, would come follow, pierce the mound in several places to a depth at least of 12", then apply an aqueous insecticide solution to the flagged mound. This technique would be vastly advantageous over insecticide granule techniques or baiting techniques since fire ants could be exterminated within hours, or even minutes, from entire swaths of infested land.

It is further anticipated that similar techniques can be employed to control any number of insect pests, including termites, wasps, fleas or cockroaches. In a similar manner, targeted colonies of insects, or targeted areas of infestation could be treated with a spray of knockout agent mist, and then soon thereafter the same targeted sites can be treated with an effective insecticide.

Finally, it is anticipate that the knockout agent, preferably trans-dichloroethylene can be used itself as a carrier for a insecticide, and that this mixture alone, or blended with other miscibles, could be applied to an area infested with insect pests. The trans-dichloroethylene/insecticide mixture will have a similar, synergistic "knockout and poison" effect on individual insects. The mixture can be applied in liquid form to insect pest colonies. The mixture should also be suitable in aerosol applications, for instance in spray cans or insect "bombs." It can be especially effective for fumigating homes infested with termites, fleas or cockroaches.

Tests

These tests were conducted on active fire ant mounds located primarily upon an acre tract of residential property in Lake Charles, La.

In the first test, a mixture of 1 part trans-dichloroethylene to 2 parts vegetable oil (liquid Crisco® brand vegetable oil) was used. A fire ant colony that had established itself within a 2-gallon flowerpot was treated with approximately 1 cup of a trans-dichloroethylene/vegetable oil mixture. The technique involved pouring the liquid mixture onto the surface of the targeted fire ant mound. Observations of fire ant activity were made upon application and following application of the mixture. Afterward, the contents of the infested flower pot were emptied upon a flat, ply-wood surface and dissected. The following results of individual fire ant activity within the treated soil were observed:

TEST 1-RESULTS

| | |
|---|---|
| Upon application of 1 cup of trans-dichloroethylene/oil mixture into 2-gallon flowerpot infested with fire ants | No individual fire ant activity was observed on the surface of the soil in the pot. |
| Upon emptying contents of 2-gallon flowerpot onto flat plywood surface. | No individual fire ant activity observed. Numerous (i.e. hundreds) of individual fire ants observed in an inert, apparently lifeless state. |
| 1 hour after emptying the contents of 2-gallon flowerpot onto flat ply-wood surface. | Many individual fire ants observed slowly moving and crawling about the soil and ply-wood surface. |

-continued

TEST 1-RESULTS

| | |
|---|---|
| 24 hours after emptying contents of 2-gallon flower pot onto flat ply-wood surface | All individual fire ants have vacated the soil and plywood surface. New fire ant mounds observed beginning to form in the grass-covered vicinity of the plywood surface. |

Conclusions: When fire ants are exposed to a knockout agent such as trans-dichloroethylene, the fire ants were not immediately killed. They were simply immobilized, or "knocked out." When the trans-dichloroethylene evaporates, and individual ants are no longer exposed to the vapors, within approximately 30 minutes the ants appear to revive and resume their normal activities. Results from this experiment indicate that trans-dichloroethylene rapidly evaporates from treated soil that is exposed to the open air. It is believed that trans-dichloroethylene, in small dosages, and for short periods of exposure, is not itself toxic to fire ants.

In the second test, the products Spectracide®, Enforcer®, and Eliminator® were tested, each separately and by itself with no trans-dichloroethylene mixture employed. All of these products are comprised of granules containing a water-soluble insecticide compound—typically Diazinon®. Following package instructions, suitable amounts of the individual products from freshly opened packages were sprinkled upon the surface of active fire ant mounds ≧12-inches in surface diameter. Then, following package instructions, the individual fire ant mounds were gently sprinkled with at least 1 gallon of water at ambient temperature (the outside temperature was between 85°–95° F.). The fire ant mounds were not excavated, as in the first test, but the following results were observed:

TEST 2-RESULTS

| | |
|---|---|
| Upon application of insecticide granules | Substantial, vigorous activity of individual fire ants observed upon surfaces of mounds. Fire ants appear to be swarming in typical fashion upon being disturbed. |
| Upon application of 1 gallon or more of water to the granules upon the surface of the mound. | Individual fire ants that had settled down somewhat after application of the granules again observed swarming upon surfaces of mounds when disturbed by water. |
| 24 hours after completed application of granule-water combination. | No individual activity observed upon the treated mounds, nor within treated mounds when dug into. However, new fire ant colonies observed forming mounds in the near vicinity of each treated mound. |

Conclusions: While the granule-based insecticides appear to kill most individual fire ants in a treated colony, the substantial activity of the individual fire ants upon application of both the granules and the water indicates that the procedure serves initially to aggravate and perhaps alarm the colony before the poison can take effect. Formation of numerous new fire ant colonies suggests that a substantial number of individual fire ants, along with their queens, are able to flee targeted areas before the insecticide completes it's goal and establishes new colonies.

In the third test, a combination of the techniques employed in the first and second tests were used. First 16 targeted fire ant mounds, 12-inches in surface diameter, were treated with a mixture of approximately 1 part trans-dichloroethylene to 2 parts peanut oil. Note: Only ¼ pint of the trans-dichloroethylene mixture was used, as opposed to the 1 cup of mixture used in Test 1. Then suitable amounts of insecticide granules (Eliminator®) were applied to these mounds in accordance with package directions. Finally, at least 1 gallon of water at ambient temperature (approximately the same temperature as in Test 2) was applied to the targeted mounds in accordance with package directions. Most of the granules appeared to dissolve, carrying poison into the colony. Observations of fire ant activity were made upon the surface of each of these targeted fire ant mounds and in the near vicinity of each of the targeted mounds. One of the larger mounds was excavated, and a plug of soil approximately 12"×12"×13" was removed and dissected upon a flat ply-wood surface. A smaller sample of this plug was spread upon a flat plastic surface and taken indoors for further observation. The following results were observed:

TEST 3-RESULTS

| | |
|---|---|
| Upon application of ¼ cup trans-dichloroethylene/peanut oil mixture to the surface of a fire ant mound. | No individual fire ant activity observed upon surface or in vicinity of the mound. |
| Upon application of insecticide granules. | No individual fire ant activity observed upon surface or in vicinity of the mound. |
| Upon application of 1 gallon or more of water. | No individual fire ant activity observed upon surface or in vicinity of the mound. |
| 5 hours after complete treatment of the 16 unexcavated mounds. | No individual fire ant activity observed upon surface, or in near vicinity of the treated mounds. |
| Upon excavation of 1 of the treated mounds (12" × 12" × 13" plug of soil) 24 hours after initial treatment. | No individual fire ant activity observed. Numerous (hundreds to thousands) of adult fire ants observed dead. Numerous fire ant larvae observed dead. Numerous fire ant eggs observed, presumed dead. Fire ant queen observed dead in the 13" (deepest portion) of the soil. |
| 5 hours after excavation of 1 of the treated mound. | No individual fire ant activity observed in both larger portion of excavated plug left outside, nor in smaller portion of excavated plug taken indoors. All adult, larvae, eggs and queen fire ant dead. |
| 24 hours after treatment of both excavated and unexcavated mounds. | No individual fire ant activity upon surface of in the near vicinity of unexcavated mounds. No individual fire ant activity within soil of excavated mound, All individual adult, larvae, eggs, and queen in excavated mound still appear dead. |

Conclusions: The dual procedure of first applying a trans-dichloroethylene mixture, even in the very small amount of ¼ pint of a ⅓:⅔ trans-dichloroethylene to oil blend, and of next applying the insecticide granules and water in accordance with package instructions appeared to exterminate the entire targeted fire ant colony. While extermination of an entire colony appeared substantially complete within 5 hours, excavation of one of the larger colonies proved that the extermination process was indeed effective 24 hours after treatment. Since no new fire ant colonies appeared to form in the near vicinity of the treated mounds within 24 hours of initial treatment, it appears that this dual-treatment procedure is more effective than either the trans-dichloroethylene mixture or the granule-water technique alone.

In the fourth test, a combination of techniques was again employed, as in the third test. However, instead of using a granule-type insecticide, a simple liquid solution of insecticide was used (a solution of 2 ounces of liquid concentrate of Diazinon®—the active ingredient in Spectracide®—and two gallons of water, in accordance with package instructions, was used on the first day). An active fire ant mound approximately 12 inches in surface diameter was first treated with approximately ¼ pint of a 1-part trans-dichloroethylene:2-parts Crisco® brand liquid vegetable oil. Within three minutes, five holes 12" deep were punctured into the targeted fire ant mound with a slender steel shaft. Then, approximately 1 gallon of the Diazinon® solution was poured upon the targeted fire ant mound. Observations of fire ant activity were made upon the surface of the targeted fire ant mound and in the near vicinity of the mound. Three hours later, the mound was excavated, and a plug of soil approximately 12"×12"×12" was removed and dissected. Observations of individual fire ant activity within the excavated plug of soil were made. Similar treatment techniques and observations were made upon four more active fire ant mounds the following day, only this time using as poison an aqueous solution made by extracting poison from Spectracide® granules. Three of these mounds targeted on the second day were first treated with the trans-dichloroethylene mixture before applying the poison. The fourth mound treated on the second day was simply wetted first with the aqueous solution of Spectracide® made from the Spectracide® granules, then re-wetted with the poison solution after 5 holes 12" deep had been punctured into the mound. The four fire ant mounds treated on the second day were excavated and dissected at their original locations on the lawn. The following results were observed:

TEST 4-RESULTS

| | |
|---|---|
| Upon applying the trans-dichloroethylene/oil mixture to the targeted mound (day 1). | No individual fire ant activity observed upon surface of mound. |
| Upon puncturing the targeted mound in 5 places (day 1). | No individual fire ant activity observed upon surface of the mound, or within holes made by punctures. |
| Upon applying the Diazinon ® solution to the targeted mound. | No individual fire ant activity observed upon surface of the mound, or within holes made by punctures. |
| Upon excavating a 12" × 12" × 12" plug of soil from the treated fire ant mound (day 1). | No individual fire ant activity observed Numerous (hundreds to thousands) of adult fire ants observed dead. Numerous fire ant larvae observed dead. Numerous fire ant eggs observed, presumed dead. Fire ant queen observed dead in the deepest portion of the soil. |
| Upon applying the trans-dichloroethylene/oil mixture to three targeted mounds (day 2). | No individual fire ant activity observed upon surface of the mound. |
| Upon puncturing the three targeted mounds in 5 places (day 2). | No individual fire ant activity observed upon surface of the mound, or within holes made by punctures. |
| Upon applying the Spectracide ® solution to the three targeted mounds (day 2). | No individual fire ant activity observed upon surface of the mound, or within holes made by punctures. |
| Upon excavating the three targeted mounds (day 2). | No individual fire ant activity observed. Numerous (hundreds to thousands) of adult fire ants observed dead. Numerous fire ant larvae observed dead. Numerous fire ant eggs observed, presumed dead. Fire ant queen observed dead. |
| Upon applying an initial Spectracide ® solution to the fourth targeted mound (day 2). | No data |
| Upon puncturing the fourth targeted mound in 5 places (day 2). | No data |
| Upon applying a second dose of Spectracide ® solution to the fourth targeted mound (day 2). | No data |

Conclusions: These tests indicate that a treatment technique involving the steps of first wetting an active fire ant mound with a trans-dichloroethylene mixture, then puncturing the mound, then applying suitable amounts of an aqueous solution of insecticide, were efficient and highly effective for eradicating fire ant colonies. Aqueous insecticide solutions either of liquid Diazinon ® or of solutions prepared by extracting poison from Spectracide ® granules appeared to be equally effective in killing individual insects in a targeted colony that was first treated with the trans-dichloroethylene mixture. However, fire ant colonies treated with only aqueous insecticide solutions, even twice, with holes punctured deep into the mound, did not appear effective in eradicating substantially all individual insects within the colony.

In the fifth test (conducted 10 months after the fourth test) an active fire ant mount was treated with a trans-dichloroethylene/biodegradable oil mixture alone. No additional insecticide, such as Diazinon®, was added to the fire ant mound. To ensure that the targeted mound was active, a shallow impression approximately 1 inch deep and 3 inches in diameter was made into the top of the mound. Ants swarmed upon the surface and around the vicinity of the mound following the disturbance. After the ants were allowed to settle down, the entire surface of this mound was wetted with a mixture comprised of one part by volume trans-dichloroethylene to two parts by volume vegetable oil (Crisco® brand). After ten minutes, another shallow impression approximately 1 inch deep and 3 inches in diameter was made into the top of the mound, but observed no ant activity. The inventor made observations of the targeted fire ant mound over the next ten and one-half (10.5) hours, including excavating a 12×12×12 inch plug of soil from the targeted fire ant mound. Afterward, the inventor replaced the excavated plug in its original location and covered the surface with dead St. Augustine grass to a depth of approximately three inches. The treated mound was observed the following day with the following results:

TEST 5-RESULTS

| | |
|---|---|
| Upon wetting the fire ant mound with the ⅓ trans-dichloroethylene, ⅔ vegetable oil mixture | Few individual ants emerged from the surface, 3 or 4 with wings. All these individuals either "passed out" or quickly re-entered the mound. |
| Upon making a depression approximately 1 inch deep and 3 inches in diameter into the surface of the mound ten minutes after initial treatment. | No fire ant activity observed within the depression or anywhere else upon or within the vicinity of the mound. All individuals observed were completely inert. Numerous white eggs observed in the depression. |
| Upon inspection of the mound two hours after initial treatment. | Dozens of fire ants observed moving about the surface of mound in a lethargic manner. Some individuals moving lethargically also detected just outside the perimeter of the hill. |
| Upon inspection of the mound seven and one-half (7.5) hours after initial treatment. | Approximately two dozen completely inert individual ants observed upon the surface of the mound. Many more individuals observed moving about the surface of the mound and around the perimeter. |
| Upon making a hole in the mound approximately two inches deep and three inches in diameter seven and one-half (7.5) hours after initial treatment. | Significant ant activity observed. Individual ants observed swarming from the hole. |
| Upon excavating a 12" × 12" × 12" plug of soil from the treated fire ant mound ten and one-half (10.5) hours after initial treatment. | Very many (i.e. hundreds to thousands) of individual fire ants observed swarming upon and from within the excavated plug of soil. Perhaps 25–30 dead individuals observed near the surface upon which mixture had been sprinkled. No detectable odor of trans-dichloroethylene in the excavated plug of soil, or in smaller samples of soil taken from plug for closer inspection. Ants were observed moving about the surface of the mound and around the perimeter. |

-continued

TEST 5-RESULTS

| | |
|---|---|
| Upon re-inspecting the plug of soil (i.e. the excavated fire ant mound) 16 hours after it had been returned to original location. | Very many (i.e. hundreds to thousands) of individual fire ants swarmed across the surface of the mound when the dead grass covering was brushed away. |

Conclusions: These tests indicate that the trans-dichloroethylene mixture itself while it may kill relatively few individual fire ants, is not capable of killing significant numbers of individual ants in a targeted mound. Instead, the mixture has the effect of immobilizing or "knocking out" individual ants temporarily (presumably for as long as individual fire ants are exposed to trans-dichloroethylene vapors). These tests further indicate that, when a mixture of trans-dichloroethylene and biodegradable oil is sprinkled upon a fire ant mound, in a reasonably short period of time the trans-dichloroethylene will evaporate and escape from the targeted mound. This is clearly evidenced by the fact that, within two hours of treatment with a trans-dichloroethylene-oil mixture, individual fire ants were observed reviving in significant numbers and moving about the targeted mound.

In the sixth test, two active fire ant mounds were treated with a one part by-volume trans-dichloroethylene to two parts by-volume biodegradable oil mixture, followed by dousing the treated mound with ambient-temperature water. No additional poison, such as Diazinon®, was used. Two active fire ant mounds approximately 6–8 inches in diameter were targeted. At 7:00 AM both mounds were wetted with the trans-dichloroethylene/oil mixture, one more thoroughly than the other. Five minutes later, the mounds were punctured in several places to a depth of 8–10 inches and observed for ant activity. None was detected. Then both treated mounds were thoroughly soaked with fresh, ambient-temperature water (approximately one-half (½) gallon each). Over the next nine hours both targeted mounds were inspected, including excavating plugs of soil from each mound approximately 10×10×14 inches in size. The following results were observed:

TEST 6-Results

| | |
|---|---|
| Upon wetting the mounds with a trans-dichloroethylene/ biodegradable oil mixture. | No significant fire ant activity observed. |
| Upon puncturing the targeted mounds with a slender shaft to a depth of 8–10 inches. | All individual fire ants detected were completely inert, as if "knocked out." |
| Upon dousing each mound with approximately one-half (½) gallon fresh water approximately five minutes after initial treatment. | No fire ant activity observed. |
| Upon observing the targeted mounds two hours after initial treatment. | Numerous (i.e. dozens) of fire ants observed crawling "lethargically" upon surface of the mounds and around the perimeter. Many inert individual ants detected within hole that had been punctured into mound. |
| Upon excavating and dissecting a 10" × 10" × 14" plug of soil from the first, more heavily treated mound. | No detectable odor of trans-dichloroethylene in soil. Numerous inert individual fire ants detected in deepest portion of the plug. Two larger ants with striped posteriors detected in this portion, also inert. Large numbers (i.e. dozens to hundreds) of individual fire ants detected in the 8"–10" portion of the plug, inert and apparently dead. However, throughout the plug significant numbers (i.e. hundreds) of live fire ants observed crawling about. Most active |

TEST 6-Results

| | |
|---|---|
| | individuals observed near the surface of the plug. Also, significant fire ant activity observed around the perimeter of the plug prior to excavation. |
| Upon inspecting the excavated plug five hours after it had been removed, dissected spread upon a ply-wood surface. | Soil from plug had significantly dried, due to exposure to sunlight and air. Active fire ants observed crawling about the soil and ply-wood. Large numbers (i.e. dozens to hundreds) of inert fire ants detected in clusters within the dissected portions of the plug (all but top 3" of plug were dissected). Three large ants with striped posteriors observed moving antennae and legs, though otherwise laying upside down. |
| Upon excavation and dissection of the second less-heavily treated mound eight hours after initial treatment. | Numerous (i.e. dozens to hundreds) of very active fire ants detected swarming throughout soil. Also, hundreds of active fire ants rapidly moving in around hole from which plug was taken. Many clusters of inert individual ants detected within plug (comprising from dozens to hundreds of individuals). |

Conclusions: Trans-dichloroethylene blended with a biodegradable oil and applied to the surface of an active fire ant mound, will "knock out" fire ants within the mound in approximately 3 to 10 minutes. However, the trans-dichloroethylene blend will not effectively kill the fire ants in the mound. While it kills a very small percentage of individual ants within the colony, the trans-dichloroethylene only serves to "knock out" the great majority of fire ants for as long as they are exposed to the trans-dichloroethylene. The quantity of trans-dichloroethylene blend applied affects the number of ants that are actually killed; the more trans-dichloroethylene blend applied, the more individual ants will not revive, once put to sleep by the compound. After several hours, the trans-dichloroethylene effectively evaporates from the treated fire ant mound soil. This evaporation process is accelerated by exposure to sunlight, and also by exposure to air (as when the mound is excavated, or at least the soil is turned). Finally, the application of water to a fire ant mound that has been treated with a trans-dichloroethylene/oil blend affects the evaporation rate of the trans-dichloroethylene. Apparently, it takes longer for the trans-dichloroethylene to evaporate when water has been applied to the treated mound. After several hours, however, especially when exposed to sunlight, the trans-dichloro ethylene will effectively evaporate from a fire ant mound that has even been doused with water. However, the procedure of exterminating fire ants within their active mound colonies is best accomplished on dry, sunny days. By performing the extermination technique in accordance with this invention on warm, sunny days, there is very little possibility that trans-dichloroethylene will contaminate soil or ground-water. Furthermore, treatment on sunny days ensures successful, accurate targeting of the fire ant colony with both the trans-dichloroethylene blend and a suitable poison, with no risk of dilution by rainwater.

In the seventh test, active fire ant colonies were treated with methanol and then with a mixture of methanol plus trans-dichloroethylene. Additionally, an aqueous Diazinon® solution was applied to a targeted mound following application of the latter mixture. First, an active fire ant mound, approximately 5 inches in diameter, was treated with enough methanol to wet the surface of the mound. Fire ants were observed exiting the mound upon application of the methanol. After swarming for several minutes the ants eventually retreated into the mound, visibly unaffected by the methanol. Then a solution of three parts methanol to one part trans-dichloroethylene was applied to the surface of a second fire ant mound approximately 8 inches in diameter. No ants swarmed upon the surface of the mound upon application of the solution. After five minutes, the second mound was pierced in several places with a steel shaft. A Diazinon® solution was then applied to the mound. At no time were ants observed exiting the second mound. On the following day, upon excavation of the second mound, total kill of the colony was observed.

| TEST 7-RESULTS | |
|---|---|
| Upon wetting a fire ant mound with pure ethanol | Significant fire ant activity observed upon surface of the mound. |
| Upon observing the mound for a period of several minutes after application of methanol. | Fire ant activity subsides as ants gradually return into the mound. No fire ant activity observed. |
| Upon wetting a second fire ant mound with a one part trans-dichloroethylene to three parts methanol by volume solution. | No fire ant activity observed. |
| Upon piercing the second fire ant mound with a steel shaft five minutes after application of the solution | No fire ant activity observed. |
| Upon application of a Diazinon ® and water solution to the second mound. | No fire ant activity observed. |
| Upon excavating the second fully treated mound on the following day. | No individual fire ant activity observed within the mound. All adult, larvae, eggs and queen fire ant observed dead. |

Conclusions: This test evidences that trans-dichloroethylene, blended with methanol, will effectively knock out fire ants within a targeted mound. Methanol serves as a relatively inexpensive miscible carrier for trans-dichloroethylene, but it does not serve to knockout fire ants.

In eighth and ninth tests, the method of the seventh test was duplicated using two other alcohols, namely ethanol and isopropanol. When solutions of ethanol and water or isopropanol and water were applied to the surface of a live fire ant colony, ants were observed swarming upon the wetted surface of either mound. Within minutes these ants returned into the mounds. Yet, when solutions of one part trans-dichloroethylene to three parts ethanol or isopropanol respectively were applied to the surface of live fire ant colonies, no fire ant activity was observed upon the surface of either of these mounds, nor upon puncturing the mounds, nor upon application of a Diazinon® and water solution to the mounds. Upon excavation of both of the fully treated mounds on the following day, total kill of both colonies was observed.

| TEST 8-RESULTS | |
|---|---|
| Upon wetting a fire ant mound with an ethanol and water solution. | Significant fire ant activity observed upon the surface of the mound. |
| Upon observing the mound for a period of minutes after application of the ethanol and water solution. | Fire ant activity subsides as ants gradually return inside the mound. |
| Upon wetting a second fire ant mound with a one part trans-dichloroethylene to three parts anhydrous ethanol by volume solution. | No fire ant activity observed. |
| Upon piercing the second fire ant mound with a steel shaft five minutes after application of the solution. | No fire ant activity observed. |
| Upon application of a Diazinon ® and water solution to the second mound. | No fire ant activity observed. |
| Upon excavating the fully treated second mound on the following day. | No individual fire ant activity observed within the mound. Total kill of all adults, larvae, eggs and queen observed. |

| TEST 9-RESULTS | |
|---|---|
| Upon wetting a fire ant mound with an isopropanol and water solution. | Significant fire ant activity observed upon the surface of the mound. |
| Upon observing the mound for a period of minutes after application of the isopropanol and water solution. | Fire ant activity subsides as ants gradually return inside the mound. |
| Upon wetting a second fire ant mound with a one part trans-dichloroethylene to three parts isopropanol solution by volume. | No fire ant activity observed. |
| Upon piercing the second fire ant mound with a steel shaft five minutes after application of the solution. | No fire ant activity observed. |
| Upon application of a Diazinon ® and water solution to the second mound. | No fire ant activity observed. |
| Upon excavating the fully treated mound on the following day. | No individual fire ant activity detected within the mound. Total kill of all adults, larvae, eggs and queen observed. |

Conclusions: This evidences that trans-dichloroethylene, blended with either anhydrous ethanol or anhydrous isopropanol, will effectively knock out fire ants within a targeted mound. Both of these alcohols may serve as relatively inexpensive miscibles for trans-dichloroethylene, but neither serves to knock out fire ants.

In a tenth test an active fire ant colony was treated with a temporarily emulsified mixture of 15 parts trans-dichlorethylene to 85 parts water by volume. Additionally, an aqueous Diazinon® solution was applied to the targeted mound. First, an active fire ant mound, approximately 6–8 inches in diameter was treated with enough of the emulsified mixture to wet the surface of the mound. No fire ants were observed exiting the mound upon application of the mixture. After five minutes, the mound was pierced in several places with a steel shaft. A Diazinon® solution was then applied to the mound. At no time were ants observed exiting the second mound. On the following day, upon excavation of the mound, total kill of the colony was observed.

| TEST 10-RESULTS | |
|---|---|
| Upon wetting a fire ant mound with a fifteen parts trans-dichloroethylene to eighty-five parts water by volume emulsified mixture. | No fire ant activity observed. |
| Upon piercing the targeted ant mound with a steel shaft five minutes after application of the emulsified mixture. | No fire ant activity observed. |
| Upon application of a Diazinon ® and water solution to the targeted mound. | No fire ant activity observed. |
| Upon excavating the fully treated mound on the following day. | No individual fire ant activity detected within the mound. Total kill of all adults, larvae, eggs and queen observed. |

Conclusions: This test shows that an emulsified mixture of trans-dichloroethylene and water will effectively knock out all individual fire ants within a colony. Water serves as an inexpensive carrier for the trans-dichloroethylene. While the emulsified mixture of trans-dichloroethylene and water is only temporary in that the two components will separate in time if left undisturbed, vigorous shaking is sufficient to emulsify the mixture and make it suitable for knocking out a fire ant colony.

In the eleventh and twelfth tests very large, very active fire ant colonies was treated with emulsified tri-component mixtures of trans-dichlorethylene, water and Diazinon® and then with emulsified mixtures of trans-dichloroethylene and water followed by treatment with a Diazinon® and water solution. In both the emulsified mixtures, the transdichloroethylene-to-water ratio was 15:85 parts by volume. In the tri-component mixture, an additional ounce of Diazinon® was added to a gallon of the trans-dichloroethylene and water emulsion (the recommended ratio of Diazinon® per gallon of water).

In the eleventh test, two mounds were wetted with the tri-component mixture. The first mound was approximately 6 inches in diameter, while the second mound was much larger at 18 inches in diameter. A few fire ants were observed exiting either mound upon application of the mixture, but these individuals fell dormant in seconds. After five minutes, the mound was pierced in several places with a steel shaft. More of the tri-component mixture was poured into either mound. On the following day, both of these mounds were excavated. The smaller, more heavily treated mound experienced a total kill of all fire ant individuals. However, perhaps ten percent of the fire ant individuals in the larger, less heavily treated mound were still alive, though moving lethargically.

In the twelfth test, an extremely large and active fire ant mound, approximately 36 inches in diameter, was wetted with the same tri-component emulsified mixture of trans-dichloroethylene, water and Diazinon®. Five minutes later, the inventor pierced the mound in several places and filled these holes with more of the tri-component mixture. Following treatment of this mound, another even larger mound, approximately 40 inches in diameter, was wetted with a simple two-component emulsified mixture of trans-dichloroethylene and water (15:85 ratio by volume). After two minutes, deep holes were punctured into this mound and more of the two-component mixture was applied. After an additional three minutes, these holes were filled with a Diazinon® and water solution.

On the following day, both of these extremely large and hitherto active fire ant mounds were excavated. A few individual ants were still alive deep within the 36 inch mound that had been treated with the tri-component mixture. The kill ratio appeared to be around ninety-five percent. However, excavation of the second, even larger mound (40 inches in diameter) treated with the two-component knock out mixture and then with a Diazinon® solution revealed a total kill of all fire ant individuals, larvae and eggs.

| TEST 11-RESULTS | |
|---|---|
| Upon wetting two active fire ant mounds, one 6 inches in diameter and the other 18 inches in diameter, with a tri-component emulsified mixture of trans-dichloroethylene, water and Diazinon ®. | Slight individual fire ant activity upon the surface of either mound following initial wetting of the mound. These individual ants fall dormant within seconds. No additional fire ant activity observed upon either mound. |
| Upon piercing both mounds with a steel shaft five minutes after applying the tri-component mixture. | No fire ant activity observed. |
| Upon further application of the tri-component mixture to the pierced mounds. | No fire ant activity observed. |
| Upon excavating both mounds on the following day. | Total kill of all individual ants, larvae and eggs in the smaller, 6-inch mound. Approximately 90% kill ratio observed in the larger 18-inch mound. Surviving ants detected only in the deepest part of the mound (approximately 14 inches deep). These ants observed moving lethargically. |

| TEST 12-RESULTS | |
|---|---|
| Upon wetting an extremely large, active fire ant mound (approximately 36 inches in diameter) with the tri-component mixture of trans-dichloroethylene, water and Diazinon ® (15:85 parts by volume of the first two components, one ounce of the third component). | Slight individual fire ant activity upon the surface of the mound following initial wetting of the mound. These individual ants fall dormant within seconds. No additional fire ant activity observed upon either mound. |
| Upon piercing holes into the 36 inch mound five minutes after wetting with the tri-component mixture and then filling the holes with more of the tri-component mixture. | No fire ant activity observed. |
| Upon wetting a second, extremely large and active fire ant mound (approximately 40 inches in diameter) with a two-component emulsified mixture of trans-dichloroethylene and water (15:85 parts by volume). | No fire ant activity observed. |
| Upon piercing holes into the 40 inch mound two minutes after initial wetting. | No fire ant activity observed. |
| Upon filling these holes in the second mound with more of the two-component mixture. | No fire ant activity observed. |
| Upon soaking the 40 inch mound with a Diazinon ® and water solution three minutes after the second treatment with the two-component mixture of trans-dichloroethylene and water. | No fire ant activity observed. |
| Upon excavating the first 36 inch mound on the following day. | Approximately 95 percent kill ratio observed. A few individual fire ants observed moving lethargically in the deepest portion of the excavated mound (approximately 16–18 inches deep). |
| Upon excavating the second 40 inch mound on the following day. | No fire ant activity observed. Total kill of all individual fire ants within the entire mound observed. |

Conclusions: These tests show that a tri-component mixture of trans-dichloroethylene, water and Diazinon ® may effectively achieve the substantially total kill of all individual insects within a relatively small fire ant colony. However, extremely large colonies of fire ants are more effectively eradicated utilizing the two-component trans-dichloroethylene and water mixture first to knock out all individual fire ants within the mound before applying a separate solution of Diazinon ® and water. Without completely knocking out all individual fire ants within the depths of a very large mound, some fire ants are apparently able to escape from the poison. Thus, it appears that the most essential step in practicing the subject invention is to knock out all individual fire ants completely and carefully using a trans-dichloroethylene and water mixture. Only when the entire colony has been thus immobilized can total kill of the colony be assured with a poison solution.

What is claimed is:

1. A method for eradicating an infestation of insects comprising the steps of:

a) exposing said infestation of insects to an effective amount of a knockout agent which is non-lethal to said insects when used in said effective amount which knockout agent is selected from the group consisting of cis-dichloroethylene, trans-dichloroethylene, trichloroacetaldehyde, trichloroacetaldehyde hydrate, and chloral hydrate; and b) subjecting the infestation of insects that was exposed to said knockout agent to an effective amount of an insecticide lethal to the insects.

2. The method of claim 1 wherein the knockout agent is trans-dichloroethylene.

3. The method of claim 1 wherein a diluent is provided, which diluent is one in which the knockout agent, the insecticide, or both, are at least partially soluble or at least partially miscible.

4. The method of claim 1 wherein the insecticide is selected from the group consisting of: a) organochlorines, b) organophosphates, c) organosulfurs, d) carbamates, e) dinitrophenols, f) organotins, g) pyrethroids, h) nicothinoids, i) spinosyns, j) fiproles, k) pyrroles, l) pyrazoles, m) phridazinoncs, n) quinazolines, o) benzoylureas, p) botanicals, q) synegists, r) antibiotics, s) fumigants, and t) fluorides.

5. The method of claim 4 wherein the insecticide is selected from the organophosphates.

6. A method for eradicating fire ants in an earthen fire ant mound, comprising the steps of:
   a) exposing said fire ants in an earthen mound to an effective amount of a knockout agent which is non-lethal to said fire ants when used in said effective amount which knockout agent is selected from the group consisting of cis-dichloroethylene, trans-dichloroethylene, trichloroacetaldehyde, trichloroacetaldehyde hydrate, and chloral hydrate; and
   b) subjecting the fire ants that were exposed to said knockout agent to an effective amount of an insecticide lethal to the said fire ants.

7. The method of claim 6 wherein the knockout agent is trans-dichloroethylene.

8. The method of claim 6 wherein a diluent is provided, which diluent is one in which the knockout agent, the insecticide, or both, are at least partially soluble or at least partially miscible.

9. The method of claim 6 wherein the insecticide is selected from organophosphates and hydramethlnon.

10. The method of claim 6 wherein the insecticide is selected from the group consisting of: a) organochlorines, b) organophosphates, c) organosulfurs, d) carbamates, e) dinitrophenols, f) organotins, g) pyrethroids, h) nicothinoids, i) spinosyns, j) fiproles, k) pyrroles, l) pyrazoles, m) phridazinones, n) quinazolines, o) benzoylureas, p) botanicals, q) synegists, r) antibiotics, s) fumigants, and t) fluorides.

* * * * *